United States Patent [19]

Steckel

[11] Patent Number: 4,599,090

[45] Date of Patent: Jul. 8, 1986

[54] METHOD FOR PREPARING NITROGEN- AND OXYGEN-CONTAINING COMPOSITIONS USEFUL AS LUBRICANT AND FUEL ADDITIVES

[75] Inventor: Thomas F. Steckel, Chagrin Falls, Ohio

[73] Assignee: The Lubrizol Corporation, Wickliffe, Ohio

[21] Appl. No.: 614,341

[22] Filed: May 25, 1984

Related U.S. Application Data

[62] Division of Ser. No. 244,946, Mar. 18, 1981, Pat. No. 4,477,362.

[51] Int. Cl.$^4$ ............................................. C10L 1/22
[52] U.S. Cl. ............................................. 44/63; 44/72
[58] Field of Search ................................. 44/63, 72

[56] References Cited

U.S. PATENT DOCUMENTS

| | | | |
|---|---|---|---|
| 2,160,058 | 5/1939 | Covert | 260/583 |
| 2,645,659 | 7/1953 | Morris et al. | 260/488 |
| 2,695,270 | 11/1954 | Jefferson et al. | 252/8.7 |
| 3,121,115 | 2/1964 | Meuly | 260/570.5 |
| 3,250,794 | 5/1966 | Mod et al. | 260/404 |
| 3,268,447 | 8/1966 | Dickey et al. | 252/33.4 |
| 3,714,259 | 1/1973 | Lichtenwalter et al. | 260/583 P |
| 3,753,912 | 8/1973 | Nankee et al. | 252/77 |
| 3,779,920 | 12/1973 | Devries | 252/33.4 |
| 3,799,876 | 3/1974 | White et al. | 252/51.5 |
| 4,036,881 | 7/1977 | Brennan et al. | 260/583 P |
| 4,044,053 | 8/1977 | Brennan et al. | 260/583 P |
| 4,103,087 | 7/1978 | Brennan | 544/78 |
| 4,152,353 | 5/1979 | Habermann | 260/585 B |
| 4,153,581 | 5/1979 | Habermann | 252/472 |
| 4,168,242 | 9/1979 | Soula | 872/941 |
| 4,386,939 | 6/1983 | Lange | 44/63 |

FOREIGN PATENT DOCUMENTS

| | | |
|---|---|---|
| 676849 | 8/1952 | United Kingdom . |
| 763344 | 12/1956 | United Kingdom . |
| 993044 | 5/1965 | United Kingdom . |
| 1124696 | 8/1968 | United Kingdom . |
| 1164783 | 9/1969 | United Kingdom . |
| 1203036 | 8/1970 | United Kingdom . |
| 1422230 | 1/1976 | United Kingdom . |
| B1426707 | 3/1976 | United Kingdom . |
| 1435538 | 5/1976 | United Kingdom . |
| 1430032 | 7/1977 | United Kingdom . |

OTHER PUBLICATIONS

Chemical Abstracts–87:5367f.

*Primary Examiner*—Y. Harris-Smith
*Attorney, Agent, or Firm*—Denis A. Polyn; Forrest L. Collins; Karl Bozicevic

[57] ABSTRACT

Nitrogen- and oxygen-containing compositions prepared by reacting, in the presence of an acid catalyst, (A) at least one aliphatic hydroxy compound of the formula $$R^1(OH)_x$$

wherein $R^1$ is an aliphatic hydrocarbon-based radical and x is an integer which is at least 1, with (B) at least one (tertiary amino) alkanol useful as lubricant and fuel additives. Also disclosed are concentrates of these compositions and lubricants and fuels containing these compositions.

43 Claims, No Drawings

METHOD FOR PREPARING NITROGEN- AND OXYGEN-CONTAINING COMPOSITIONS USEFUL AS LUBRICANT AND FUEL ADDITIVES

This application is a division of copending application Ser. No. 244,946, now U.S. Pat. No. 4,477,362, filed Mar. 18, 1981.

FIELD OF THE INVENTION

This invention relates to nitrogen- and oxygen-containing compositions. These compositions are useful as lubricant and fuel additives. Additionally, this invention relates to concentrates of these compositions and to lubricant and fuel compositions comprising these compositions. This invention also relates to a method for preparing these nitrogen- and oxygen-containing compositions from aliphatic alcohols and (tertiary amino) alkanols.

SUMMARY OF THE INVENTION

A principal object of the present invention is to provide novel nitrogen- and oxygen-containing compositions as well as processes for making them.

Another principal object of the present invention is to provide novel nitrogen- and oxygen-containing compositions which exhibit antioxidant, anticorrosive, detergent and dispersant properties.

Another object is to provide novel concentrates comprising these novel nitrogen- and oxygen-containing compositions.

Still another object is to provide novel lubricant and fuel compositions containing these novel nitrogen- and oxygen-containing compositions.

An additional object is to provide novel compositions which are effective antioxidants, anticorrosives, detergents, and/or dispersants in lubricants and fuels when incorporated therein.

These and other objects of the invention are accomplished by providing a method for preparing a nitrogen- and oxygen-containing composition which comprises reacting, in the presence of an acidic catalyst, (A) at least one aliphatic hydroxy compound of the formula $R^1(OH)_x$ wherein $R^1$ is an aliphatic hydrocarbon-based radical and x is an integer which is at least 1, with (B) at least one (tertiary amino) alkanol.

The $R^1(OH)_x$ used to prepare the compositions of this invention may be any one of a wide variety of hydroxy compounds such as monohydric and polyhydric alcohols, and the like. Examples of such hydroxy compounds are alkanols, alkanediols, alkenols, alkenediols, arylalkanols, polyethylene glycols and the monoether derivatives thereof.

In the preferred compounds according to this invention, $R^1$ is an aliphatic hydrocarbon-based radical. As used herein, the term "aliphatic hydrocarbon-based radical" denotes a radical having a carbon atom directly attached to the remainder of the molecule and having predominantly aliphatic hydrocarbon character within the context of this invention. Such radicals include the following:

(1) Aliphatic hydrocarbon radicals; e.g., alkyl, alkenyl, and aromatic-substituted alkyl and alkenyl radicals, and the like. Such radicals are known to those skilled in the art; examples include ethyl, propyl, butyl, pentyl, octyl, decyl, dodecyl, stearyl, dodecenyl and oleyl (all isomers being included).

(2) Substituted aliphatic hydrocarbon radicals; that is, radicals containing non-hydrocarbon substituents which, in the context of this invention, do not alter the predominantly aliphatic hydrocarbon character of the radical. Those skilled in the art will be aware of suitable substituents (e.g., halo, alkoxy, hydroxy, alkylthio, carbalkoxy, nitro).

(3) Hetero aliphatic hydrocarbon radicals; that is, radicals which, while predominantly aliphatic hydrocarbon in character within the context of this invention, contain atoms other than carbon present in a chain or ring otherwise composed of carbon atoms. Suitable hetero atoms will be apparent to those skilled in the art and include, for example, oxygen and nitrogen.

In general, no more than about three substituents or hetero atoms, and preferably no more than one, will be present for each 10 carbon atoms in the aliphatic hydrocarbon-based radical.

Preferably, the aliphatic hydrocarbon-based radical present as $R^1$ in the compounds of this invention is free from acetylenic and usually also from ethylenic unsaturation and contains at least 5 carbon atoms. Most often, it is an alkyl-based radical, usually an alkyl radical having about 5-40 carbon atoms. Generally, x is an integer of from 1 to 6, preferably, 1 to 4.

The term "alkyl-based radical," as used herein, denotes an alkyl radical within the description of the term "aliphatic hydrocarbon-based radical" and includes alkyl radicals analogous to the "aliphatic hydrocarbon-based radicals" described hereinabove and such radicals are alkyl-hydrocarbon radicals, substituted alkyl-hydrocarbon radicals and hetero-alkyl hydrocarbon radicals.

Compounds illustrative of $R^1(OH)_x$ where x is 2 or more are ethylene glycol, propylene glycol, trimethylene glycol, glycerol, pentaerythritol, erythritol, sorbitol, and mannitol.

Reagent (A), the hydroxy compound, is intended to include (tertiary amino) alkanols (B). However, the above discussion of $R^1$ is limited to $R^1(OH)_x$ compounds. Therefore, the above discussion concerns only $R^1(OH)_x$ which is of course generic to $(R^2)_m N \!-\!(R^3\!-\!OH)_x$. However, $(R^2)_m N \!-\!(R^3\!-\!OH)_x$ is defined and discussed in detail hereinbelow. Also, the (tertiary amino) alkanol used as reagent (A) may be the same or a different (tertiary amino) alkanol from that used as reagent (B).

The (tertiary amino) alkanol compounds useful as reagent (A) and (B) of this invention are preferably those represented by the formula

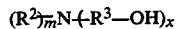

wherein
each $R^2$ is a hydrocarbon-based radical or two $R^2$ radicals taken together with the nitrogen to which each is attached to form a heterocyclic ring;
each $R^3$ is a divalent aliphatic hydrocarbon-based radical having 2-6 carbon atoms separating nitrogen from oxygen;
m is 0, 1 or 2; x is 1, 2 or 3; and m+x=3. Such heterocyclic ring radicals include, for example, morpholino, C-(alkyl substituted)morpholino, piperazino, C-(alkyl substituted) piperazino, pyrrolidino, and the like.

The hydrocarbon-based radicals of the present invention denote a radical having a carbon atom directly attached to the remainder of the molecule and having predominantly hydrocarbon character within the context of this invention. Such radicals include:

(1) hydrocarbyl radicals; that is aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical).

(2) Substituted hydrocarbon radicals, that is, radicals containing non-reactive or substantially non-hydrocarbon substituents which, in the context of this invention, do not alter the predominantly hydrocarbon character of the radical. Representative non-reactive or substantially non-reactive, non-hydrocarbon or polar substituents which can be present as a substituent include halo substituents such as chloro, fluoro, bromo, and ido; nitro; lower alkoxy such as butoxy and hexyloxy; lower alkylthio, such as methylthio, pentylthio and heptylthio. The substitution of and the nature of the substituent on the hydrocarbon-based radical is such that the essentially hydrocarbon character of the radical is not destroyed. Thus, in view of this requirement, these radicals normally have no more than two such polar or non-hydrocarbon substituents per substituted hydrocarbon radical and usually not more than one polar or non-hydrocarbon substituent for about every 10 carbon atoms in the substituted hydrocarbon radical. In other words, the substituted hydrocarbon radicals are analogous to the hydrocarbon groups discussed and exemplified above except for the presence of certain polar or non-hydrocarbon substituents which do not materially alter the predominantly hydrocarbon nature of the hydrocarbon-based radicals.

The hydrocarbon-based radicals of the invention are substantially free from acetylenic unsaturation —C≡C—. Olefinic unsaturation, if present, usually averages to about one double bond per 8 carbon atoms.

As used in the present specification and claims, the term "lower", when used in conjunction with terminology designating a chemical group such as alkyl, alkenyl, alkylene and the like, is intended to describe such groups having a total carbon atom content of up to 7. For example, "lower alkyl" includes all straight and branched chain alkyl groups of up to 7 carbon atoms.

$R^2$ will generally contain from 2 up to about 300 aliphatic carbon atoms. Compositions prepared from reagent (B) can be classified in two generally preferred classes. Those reagent (B)'s where $R^2$ contains from 2 up to about 40 carbon atoms are usually classified as non-dispersants and $R^2$ is preferably alkyl, aryl, alkaryl or arylalkyl having from about 8 to up to about 25 carbon atoms. Reagent (B)'s where $R^2$ contains from about 40 up to about 300 carbon atoms are usually classified as dispersants and $R^2$ preferably contains from about 50 up to about 250 aliphatic carbon atoms. The term "dispersant" as used herein is a composition which when added to an oil of lubricating viscosity is capable of dispersing oil-insoluble materials therein. If a material is to function as a dispersant it must usually contain a long chain hydrocarbon group of at least about 40 carbon atoms. Although these two groups are distinguishable as to their dispersant capabilities, both groups, irrespective of carbon chain length, may provide antioxidant, anticorrosive and/or detergent properties to liquid hydrocarbons.

$R^3$ is preferably an alkylene-based radical, usually an alkylene radical, having from 2 up to about 25 carbon atoms and having 2 carbon atoms separating nitrogen from oxygen.

Particularly preferred as reagent (B) are N-(hydroxyalkyl) morpholines depicted by the following formula:

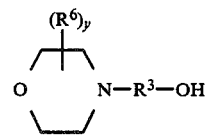

wherein $R^3$ is a divalent aliphatic hydrocarbon-based radical as defined hereinabove and $R^6$ is a lower alkyl radical of from 1 to about 4 carbon atoms and y is an integer from 0 to 4.

Examples of suitable (tertiary amino) alkanols that may be employed in the process are: 2-diethylaminoethanol, 2-(N-ethyl laurylamino)ethanol, 2-dimethylaminoethanol, 2-piperidinoethanol, 2-pyrrolidinoethanol, 2-(2,4-dimethylpyrrolidino)ethanol, 2-dimethylaminopropanol, 2-dimethylaminoisopropanol, 3-dimethylaminobutanol, 2-di-n-propylaminoethanol, 2-di-n-butylaminoethanol, 2-(2-methylpyrrolidino)isopropanol, 3-(N-methylstearylamino) propanol, 4-dimethylaminobutanol, 2-(2,6-dimethylpiperidino)ethanol, 2-(N-ethylpiperazino)ethanol, 2-morpholinoethanol, 2-thiamorpholinoethanol, N-ethyl-diethanolamine, triethanolamine, tetrakis(2-hydroxypropyl)ethylenediamine, 1,4-bis-hydroxyethyl-piperazine, 2-(di-2-ethoxyethylamino) ethanol, 2-(N-methylcyclohexylamino) ethanol, 2-(N-ethylphenylethylamino) ethanol and N-(3-morpholinopropyl) diethanolamine.

For the purposes of this invention, all nitrogen atoms contained in reagents (A) and/or (B) must be tertiary nitrogen atoms, i.e., no hydrogen atoms attached to the nitrogen.

Particularly preferred (tertiary amino) alkanols are the N-alkyldiethanolamines illustrated by the materials sold by the Armak Company under the trademark ETHOMEEN. The Ethomeens are ethoxylated fatty amines of the formula

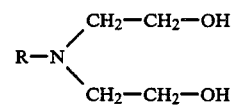

wherein R is a fatty alkyl radical derived from a fatty acid. The Ethomeens useful for the purpose of this invention include Ethomeen C/12 (alkyl radical derived from Coco fatty acid), Ethomeen O/12 (alkyl radical derived from oleic acid), Ethomeen S/12 (alkyl radical derived from soya fatty acid), Ethomeen T/12 (alkyl radical derived from tallow fatty acid) and Ethomeen 18/12 (alkyl radical derived from stearic acid).

Other (tertiary amino) alkanols useful in the preparation of the compositions of the present invention are those of the formula $R^5$—O—$R^4$—N—($R^3$—OH)$_2$ wherein $R^3$ is defined hereinabove, $R^4$ is an alkylene radical having 2 to 6 carbon atoms and $R^5$ is a hydrocarbon-based radical of about 5 to about 150 carbon atoms. These (tertiary amino) alkanols are generally prepared by the reaction of 2 moles of an alkylene oxide, e.g., ethylene oxide, propylene oxide, etc., with a primary ether amine of the formula $R^5$—O—$R^4$—NH$_2$. These primary ether amines are generally prepared by the reaction of an alcohol $R^5OH$ with an unsaturated nitrile. The $R^5$ radical of the alcohol can be a hydrocarbon-based radical, as defined earlier, or an aliphatic-, or aromatic-based radical having up to about 150 carbon atoms. Typically, and for efficiency and economy, the alcohol is a linear or branched aliphatic alcohol with $R^5$ having up to about 50 carbon atoms, preferably up to 26 carbon atoms and most preferably $R^5$ has from 6 to 20 carbon atoms. The nitrile reactant can have from 2 to 6 carbon atoms with acrylonitrile being most preferred. Ether amines are known commercial products which are available under the name SURFAM TM produced and marketed by Worth Chemical Company, Worthington, Ohio 43085. Typical of such amines are those having from about 150 to about 400 molecular weight. Preferred ether amines are exemplified by those identified as SURFAM P14AB (branched $C_{14}$), SURFAM P16A (linear $C_{16}$), SURFAM P17AB (branched $C_{17}$). The carbon chain lengths (i.e., $C_{14}$, etc.) of the SURFAMS described above and used hereinafter are approximate and include the oxygen ether linkage. For example, a $C_{14}$ SURFAM would have the following general formula: $C_{10}H_{21}$—O—$C_3H_6$—$NH_2$.

The reaction of reagents (A) and (B) requires the presence of an acid catalyst. Those catalysts useful for the purposes of this invention include mineral acids (mono-, di- and poly basic acids) such as hydrochloric acid, sulfuric acid, and phosphoric acid; organo phosphorus acids and organo sulfonic acids such as $RP(O)(OH)_2$ and $RSO_3H$; alkali metal partial salts of $H_3PO_4$ and $H_2SO_4$, such as $NaHSO_4$, $LiHSO_4$, $KHSO_4$, $NaH_2PO_4$, $LiH_2PO_4$ and $KH_2PO_4$; alkaline earth metal partial salts of $H_3PO_4$ and $H_2SO_4$, such as $CaHPO_4$, $CaSO_4$ and $MgHPO_4$; also, $Al_2O_3$ and Zeolites. Phosphoric acid is preferred because of its commercial availability and ease of handling. Also useful as catalysts for this invention are those materials which generate acids when heated in the reaction mixture, e.g., triphenylphosphite.

Although the exact nature of the reaction of reagents (A) and (B) is not known, it is believed that this reaction involves the condensation of two hydroxyl groups with the elimination of a molecule of water to form an ether. According to this stoichiometry, for example, the reaction of a di-alkyl aminoethanol and an alkyl alcohol would have the following reaction scheme

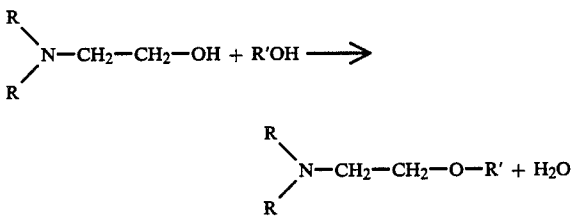

The equivalent weight of (A) and (B) is determined by dividing the molecular weight of (A) or (B) by the number of condensible hydroxyl groups contained therein. For example, the equivalent weight of a mono-hydroxy compound would be equal to its molecular weight; pentaerythritol would have an equivalent weight equal to its molecular weight (136) divided by four, i.e., 33.5; triethanolamine would have an equivalent weight equal to its molecular weight (149) divided by three, i.e., 49.7; and dibutylaminoethanol would have an equivalent weight equal to its molecular weight (174). Theoretically, the amount of water evolved for complete conversion of all the hydroxyl groups into ethers is 0.5 mole of water for each equivalent of (A) and (B) combined.

For the purposes of this invention the ratio of equivalents of reagents A:B will usually range from about 1:100 up to about 100:1, preferably from about 1:20 up to about 20:1, more preferably from about 1:10 up to about 1:1. Obviously, these ratios only apply where (A) is not the same (tertiary amino) alkanol as (B) (i.e., the self-condensation of a (tertiary amino) alkanol). The amount of catalyst necessary will fall within the range of about 0.01 up to about 20, usually from about 0.2 up to about 5 percent by weight, based on the weight of the reaction mixture of (A) and (B).

The reaction process for the preparation of the compositions of this invention is usually carried out for a period long enough for the condensation to be substantially complete, although in some instances it may be desirable not to carry out the reaction to the point of a substantially complete condensation of the hydroxyl groups. For example, one such instance would be when (A) is a (tertiary amino) alkanol of the formula $$N\text{---}(R^3\text{---}OH)_3$$

and (B) is a (tertiary amino) alkanol of the same formula. In this situation there is such a high degree of crosslinking that gelling occurs after approximately 90 percent water formation (i.e., 90 percent of the condensible hydroxyl groups have reacted to form ethers). As a result this material would be undesirable for most uses as a lubricant or fuel additive. Therefore, it is desirable to stop the reaction before gelling occurs (i.e., by lowering the reaction mixture temperature below that necessary for the reaction to proceed). Should it be desirable to stop a reaction mixture of 1 mole (3 equivalents) (tertiary amino) alkanol of the formula $$N\text{---}(R^3\text{---}OH)_3$$

at a point where half of the condensible hydroxyl groups are left unreacted, the reaction is carried out until 2.7 moles (48 parts) of water is formed.

For practical purposes, one of ordinary skill in the art could determine the extent of water formation by standard techniques such as distillation, separation, and the like. Preferably, the water of reaction is removed continuously as it is formed. The reaction period can be about 0.5 to 72 hours, but is usually 0.5 to 24 hours at a temperature of from about 140° C. up to just below the decomposition temperature of any component of the reaction mixture, usually from about 180° up to 260° C. Should any of the ingredients have a boiling point below that of the desired reaction temperature, the reaction may be conveniently carried out at super atmospheric pressures.

The reaction may be carried out in the presence of a substantially inert liquid solvent/diluent medium. This solvent/diluent medium desirably serves to maintain contact of the reactants and facilitates control of the reaction temperature. Examples of suitable solvent/diluent media include aliphatic and aromatic hydrocarbons as benzene, toluene, naphtha, mineral oil, hexane; chlorinated hydrocarbons as dichlorobenzene, and heptylchloride; ethers as methyl n-amylether, n-butylether.

As used in the specification and the appended claims, the term "substantially inert" when used to refer to solvents/diluents, and the like, is intended to mean that the solvent/diluent, etc., is sufficiently inert to chemical or physical change under the conditions in which it is used so as not to materially interfere in an adverse manner with the preparation, storage, blending and/or functioning of the compositions, additive, compound, etc., of this invention in the context of its intended use. For example, small amounts of a solvent/diluent, etc., can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

As used in the specification and the appended claims, the term "solvent/diluent medium" is intended to include those solvent/diluent media in which independently each of the reactants are soluble or stably dispersible. The term "stably dispersible" as used in the specification and the appended claims is intended to mean a composition (e.g., a single compound, a mixture of two or more compounds, etc.) is capable of being dispersed in a given medium to an extent which allows it to function in its intended manner. Thus, for example, where a composition is prepared by a reaction in an oil, it is sufficient that the reactants be capable of being suspended in the oil in a manner sufficient to allow the reaction to occur and the formation of the composition. Thus, the term "solvent/diluent medium" is understood and can be used in a conventional manner by those of ordinary skill in the art.

The compositions of this invention may be used as a lubricant additive. However, the compositions made by reacting (A) and (B) sometimes may be accompanied by the formation of by-products and/or excess solvent/diluent medium which may lessen its commercial appeal. Accordingly, these undesirable by-products and/or excess of undesired solvent/diluent medium can be separated from the compositions of this invention by techniques known in the art; e.g., filtration, evaporation (e.g., stripping), etc., to obtain a more desirable product. Alternatively, if the solvent/diluent medium is, for example, a lubricant base suitable for use in the lubricating compositions of this invention, the product can be left in the solvent/diluent medium and used to form the lubricating compositions as described below.

This invention is exemplified in the following examples. Of course, these examples are not intended as limiting this invention as modification of the examples by ordinary expedient will be readily apparent to those of ordinary skill in the art.

In all examples, unless otherwise stated, all parts are parts by weight and all percentages are derived from parts by weight.

EXAMPLE 1

A reaction mixture is prepared by the addition of 2.3 parts (0.02 mole) of phosphoric acid to 218 parts (1.6 moles) of pentaerythritol and 368 parts (2.4 moles) of triethanolamine at 125° C. under a nitrogen blanket. The reaction mixture is heated at 248°–255° C. for about 4 hours under nitrogen. A Dean-Stark trap is used to continuously remove water from the reaction mixture. A total of 58 grams of aqueous distillate is obtained. The residue is the desired condensation product having 6.21% nitrogen.

EXAMPLE 2

A reaction mixture is prepared by the addition of 2.3 parts (0.02 mole) of phosphoric acid to 146 parts (0.8 mole) of sorbitol and 119 parts (0.8 mole) of triethanolamine at 125° C. under a nitrogen blanket. The reaction mixture is heated to 254° C. in 1.5 hours and held at 254°–256° C. for 1.3 hours under nitrogen. A Dean-Stark trap is used to continuously remove water from the reaction mixture. A total of 34 parts of aqueous distillate is obtained. The reaction mixture is stripped at 155° C. under vacuum to yield the residue as the desired condensation product having 4.26% nitrogen.

EXAMPLE 3

A reaction mixture is prepared by the addition of 2.3 parts (0.02 mole) of phosphoric acid to 200 parts (1 mole) of tridecyl alcohol and 149 parts (1.0 mole) of triethanolamine at 50° C. under a nitrogen blanket. The reaction mixture is heated to 235° C. in 1.75 hours and held at 235°–240° C. for 2 hours, at 240°–255° C. for 3.5 hours under nitrogen. A Dean-Stark trap is used to continuously remove water from the reaction mixture. A total of 36 parts of aqueous distillate is obtained. The reaction mixture is filtered at 130° C. to yield a residue as the desired condensation product having 4.25% nitrogen.

EXAMPLE 4

A mixture of 864 parts (6 moles) of N-aminopropyl morpholine and 2 parts of water is heated to 130° C. Ethylene oxide, 591 parts (13.5 moles), is bubbled beneath the surface of the reaction mixture over a period of about 8 hours at 130°–145° C. The reaction mixture is stripped at 110° C. under vacuum to yield the desired N-(3-morpholinopropyl)diethanolamine as the product.

A mixture of 130 parts (0.56 mole) of the N-(3-morpholinopropyl)diethanolamine prepared above and 2.91 parts (0.28 mole) of lithium dihydrogen phosphate is heated at 220°–240° C. for 6 hours under a nitrogen blanket. A Dean-Stark trap is used to continuously remove water from the reaction mixture. A total of 9 parts of aqueous distillate is obtained. The reaction mixture is stripped at 220° C. under vacuum and then filtered to yield the desired self-condensation product having 12.79% nitrogen.

EXAMPLE 5

A mixture of 150 parts (0.65 mole) of the N-(3-morpholinopropyl)diethanolamine prepared in Example 4 and 4.42 parts (0.0325 mole) of potassium dihydrogen phosphate is heated at 260° C. for 6 hours under a nitrogen blanket. A Dean-Stark trap is used to continuously remove water from the reaction mixture. A total of 12 parts of aqueous distillate is obtained. The reaction mixture is stripped at 220° C. under vacuum and then filtered to yield the desired self-condensation product having 12.8% nitrogen.

EXAMPLE 6

The procedure for Example 5 is repeated except the potassium dihydrogen phosphate is replaced on an equimolar basis by sodium dihydrogen phosphate, the desired condensation product having 12.94% nitrogen.

EXAMPLE 7

The procedure of Example 5 is repeated except the potassium dihydrogen phosphate is replaced on an equimolar basis by sodium bisulfate, the desired condensation product having 13.4% nitrogen.

EXAMPLE 8

A mixture of 232 parts (1 mole) of the N-(3-morpholinopropyl)diethanolamine prepared in Example 4, 87 parts (0.5 mole) of (dibutylamino)ethanol and 8.6 parts (0.075 mole) of phosphoric acid is heated at 240° C. for 5 hours under a nitrogen blanket. A Dean-Stark trap is used to continuously remove water from the reaction mixture. A total of 22 parts of water is obtained. The reaction mixture is stripped at 240° C. under vacuum and filtered to yield the desired condensation product having 10.6% nitrogen.

EXAMPLE 9

A mixture of 2108 parts (24.2 moles) of morpholine and 6 parts of water is heated to 120° C. Ethylene oxide is bubbled beneath the surface of the reaction mixture over a period of about 7 hours at 120°-135° C. until a weight gain of 1100 parts is obtained. The reaction mixture is stripped at 200° C. and the residue is the desired N-morpholinoethanol product.

A mixture of 350 parts (1 mole) of a commercially available (tertiary amino) alkanol sold under the trade name Ethomeen T/12, 65.5 parts (0.5 mole) of the N-morpholinoethanol prepared above and 8.6 parts (0.75 mole) of phosphoric acid is heated to 180° C. The reaction mixture is then heated gradually over 1 hour to 240° C. The reaction mixture is held at 220°-240° C. for 4 hours. A Dean-Stark trap is used to continuously remove water from the reaction mixture. A total of 27 parts of aqueous distillate is obtained. The reaction mixture is filtered at room temperature to yield the desired condensation product having 5.18% nitrogen.

EXAMPLE 10

A reaction mixture of 350 parts (1 mole) of a commercially available (tertiary amino) alkanol sold under the trademark Ethomeen T/12, 131 parts (1 mole) of the N-morpholinoethanol prepared in Example 9 and 11.5 parts (0.1 mole) of phosphoric acid is heated to 180° C. The reaction mixture is then heated gradually over 2 hours to 240° C. The reaction mixture is then held at 220°-240° C. for 4 hours. A Dean-Stark trap is used to continuously remove water from the reaction mixture. A total of 29 parts of aqueous distillate is obtained. The reaction mixture is filtered to yield the desired product having 6.25% nitrogen.

EXAMPLE 11

A reaction mixture is prepared by the addition of 2435 parts (14.4 moles) of diphenylamine to 100 parts of zinc chloride which was melted under vacuum, then cooled to room temperature. The reaction mixture is heated to 120° C. and 663 parts (15.9 moles) of ethylene oxide is bubbled beneath the surface over a 10 hour period at 120°-140° C. The product is distilled at 180°-220° C. at 1-2 millimeters mercury to yield 2719 parts of distillate as the desired (diphenylamino)ethanol product.

A mixture of 350 parts (1 mole) of a commercially available (tertiary amino) alkanol sold under the trademark Ethomeen T/12, 213 parts (1 mole) of the (diphenylamino) ethanol prepared above and 11.5 parts (0.1 mole) of phosphoric acid is heated to 240° C. The reaction mixture is held at 220°-240° C. for 5 hours. A Dean-Stark trap is used to continuously remove water from the reaction mixture. A total of 25 parts of aqueous distillate is obtained. The product is filtered to yield the desired condensation product having 4.95% nitrogen.

EXAMPLE 12

A mixture of 191 parts (0.7 mole) of a commercially available (tertiary amino) alkanol sold under the trademark Ethomeen C/12, 150 parts (0.7 mole) of the (diphenylamino)ethanol prepared in Example 11 and 8 parts (0.07 mole) of phosphoric acid is heated at 220°-240° C. for 5 hours. A Dean-Stark trap is used to continuously remove water from the reaction mixture. A total of 18 parts of aqueous distillate is obtained. The reaction mixture is filtered at room temperature to yield the desired condensation product having 5.69% nitrogen.

EXAMPLE 13

A mixture of 130 parts (0.75 mole) of (dibutylamino) ethanol, 412 parts (1.5 moles) of a commercially available (tertiary amino) alkanol sold under the trademark Ethomeen C/12, and 12.5 parts (0.11 mole) of phosphoric acid is heated at 240° C. for 5 hours. A Dean-Stark trap is used to continuously remove water from the reaction mixture. A total of 34 parts of aqueous distillate is obtained. The reaction mixture is stripped at 240° C. under vacuum to yield a residue as the desired condensation product having 5.26% nitrogen.

EXAMPLE 14

A mixture of 66 parts (0.5 mole) of the N-morpholinoethanol prepared in Example 9, 137 parts (0.5 mole) of a commercially available (tertiary amino) alkanol sold under the trademark Ethomeen C/12, and 6.7 parts (0.05 mole) of phosphoric acid is heated to 180° C. The reaction mixture is then heated gradually over 2 hours to 140° C. The reaction mixture is held at 240° C. for 5 hours. A Dean-Stark trap is used to continuously remove water from the reaction mixture. A total of 17 parts of aqueous distillate is obtained. The reaction mixture is then stripped at 220° C. under vacuum and filtered at room temperature to yield the desired condensation product having 6.53% nitrogen.

EXAMPLE 15

A reaction mixture is prepared by the addition of 805 parts (2.27 moles) of a commercially available aliphatic substituted secondary amine sold by Armak Company under the trademark Armeen 2C and 2 parts p-toluene sulfonic acid at 120° C. under a nitrogen blanket. Ethylene oxide, 100 parts (2.27 moles), is bubbled beneath the surface of the reaction mixture over a period of 6 hours at 120°-140° C. The reaction mixture is filtered to yield the desired (tertiary amino) alkanol product.

A mixture of 159 parts (0.4 mole) of the (tertiary amino) alkanol prepared above, 109 parts (0.4 mole) of a commercially available (tertiary amino) alkanol sold under the trademark Ethomeen C/12, 4.6 parts (0.04 mole) of phosphorus acid is heated at 240° C. for 6 hours. A Dean-Stark trap is used to continuously remove water from the reaction mixture. A total of 10 parts of aqueous distillate is obtained. The reaction mixture is stripped at 200° C. under vacuum and filtered to yield the desired condensation product having 4.23% nitrogen.

EXAMPLE 16

The procedure for Example 15 is repeated except the (tertiary amino) alkanol prepared in Example 15 is replaced on an equimolar basis by (dibutylamino) ethanol, the desired condensation product having 6.18% nitrogen.

EXAMPLE 17

A mixture of 3550 parts (5 moles) of poly(isobutylene) chloride prepared by reacting a poly(isobutylene) having a number average molecular weight of about 900 with chlorine gas at 195°–205° C. until a chlorine content of 5.0 percent is obtained, 525 parts (5 moles) of diethanol amine, 1775 parts of isopropyl alcohol, 1775 parts of xylene and 419 parts (5.25 moles) of a 50% solution of sodium hydroxide is heated at 95°–98° C. for 5 hours. The reaction mixture is heated to 165° C. to remove volatiles and further stripped at 150° C. under vacuum and filtered at 150° C. to yield the desired N-poly(isobutylene)diethanol amine product.

A reaction mixture is prepared by the addition of 1.7 parts (0.015 mole) of phosphoric acid to 215 parts (0.15 equivalents of nitrogen) of the N-poly(isobutylene)diethanol amine prepared above and 18.6 parts (0.125 mole) of triethanolamine at 130° C. under a nitrogen blanket. The reaction mixture is heated to 240° C. in 2.25 hours and held at 240°–250° C. for 5 hours and at 250°–265° C. for 4 hours. A Dean-Stark trap is used to continuously remove water from the reaction mixture. A total of 12 parts of aqueous distillate is obtained. The reaction mixture is filtered at 150° C. to yield the desired condensation product.

EXAMPLE 18

A reaction mixture is prepared by the addition of 2.3 parts (0.02 mole) of phosphoric acid to 162 parts (0.6 mole) of a commercially available $C_{18}$ alcohol sold by CONOCO Chemicals under the trademark Alfol 18 Alcohol and 89 parts (0.6 mole) of triethanolamine at 105° C. under a blanket of nitrogen. The reaction mixture is heated to 240° C. in 2.3 hours and held at 240°–250° C. for 2 hours. A Dean-Stark trap is used to continuously remove water from the reaction mixture. A total of 18 parts of aqueous distillate is obtained. The reaction mixture is filtered at 135° C. to yield a filtrate as the desired condensation product.

As previously indicated, the compositions of this invention are also useful as additives for lubricants, in which they function primarily as antioxidants, anticorrosives, detergents and dispersants. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic and mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes [e.g., dodecylbenzenes, tetradecylbenzenes, dinonylbenzenes, di(2-ethylhexyl)benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants [e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.]. Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the composition of this invention sufficient to provide it with antioxidant, anticorrosive, detergent or dispersant properties. Normally this amount will be about 0.05% to about 20%, preferably about 0.1% to about 10% of the total weight of the lubricant. In lubricating oils operated under extremely adverse conditions, such as lubricating oils for marine diesel engines, the reaction products of this invention may be present in amounts of up to about 30% by weight.

The term "minor amount" as used in the specification and appended claims is intended to mean that when a composition contains a "minor amount" of a specific material that amount is less than 50% by weight of the composition.

The term "major amount" as used in the specification and appended claims is intended to mean that when a composition contains a "major amount" of a specific material that amount is more than 50% by weight of the composition.

The invention also contemplates the use of other additives in combination with the compositions of this invention. Such additives include, for example, auxiliary detergents and dispersants of the ash-producing or ashless type, auxiliary corrosion- and oxidation-inhibiting agents, pour point depressing agents, extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°-200° C.

Auxiliary ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |

-continued

| | | |
|---|---|---|
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and auxiliary corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain about 20–90% by weight of the composition of this invention and may contain, in addition, one or more other additives known in the art or described hereinabove.

The fuel compositions of the present invention contain a major proportion of a normally liquid fuel, usually a hydrocarbonaceous petroleum distillate fuel such as motor gasoline as defined by ASTM Specification D-439-73 and diesel fuel or fuel oil as defined by ASTM Specification D-396. Normally liquid fuel compositions comprising non-hydrocarbonaceous materials such as alcohols, ethers, organonitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol, and diesel fuel and ether. Particularly preferred is gasoline, that is, a mixture of hydrocarbons having an ASTM boiling point of about 60° C. at the 10% distillation point to about 205° C. at the 90% distillation point.

Generally, these fuel compositions contain an amount of the composition of this invention sufficient to impart antioxidant, anticorrosive, detergent or dispersant properties to the fuel; usually this amount is about 0.001 to about 5% (based on the weight of the final composition), preferably 0.001% to 1%.

The fuel compositions of this invention can contain, in addition to the compositions of this invention, other additives which are well known to those of skill in the art. These can include antiknock agents such as tetra-alkyl lead compounds, lead scavengers such as haloalkanes (e.g., ethylene dichloride and ethylene dibromide), deposit preventors or modifiers such as triaryl phosphates, dyes, cetane improvers, auxiliary antioxidants such as 2,6-ditertiary-butyl-4-methylphenol, rust inhibitors such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described compositions are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Pat. No. 1,396,645, British Pat. Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British patent specification No. 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0, preferably about 1 to about 10 parts of composition to 1 part ashless dispersant. In still another embodiment of this invention, the inventive additives are combined with Mannich condensation products formed from substituted phenols, aldehydes, polyamines, and substituted pyridines. Such condensation products are described in U.S. Pat. Nos. 3,649,659; 3,558,743; 3,539,633; 3,704,308; and 3,725,277.

The compositions of is invention can be added directly to the fuel to form the fuel compositions of this invention or they can be diluted with a substantially inert, normally liquid organic solvent/diluent such as mineral oil, xylene, or a normally liquid fuel as described above, to form an additive concentrate which is then added to the fuel in sufficient amounts to form the inventive fuel composition described herein. These concentrates generally contain about 20 to 90 percent of the compositions of this invention and can contain in addition any of the abovedescribed conventional additives, particularly the aforedescribed ashless dispersants in the aforesaid proportions. The remainder of the concentrate is the solvent/diluent.

The lubricant, fuel and additive concentrate compositions of this invention are exemplified by the following:

EXAMPLE A

A gasoline having a Reid vapor pressure of 8.4 psi and containing 24 parts per million parts of gasoline of the condensation product described in Example 16.

EXAMPLE B

A diesel fuel oil containing 40 parts per million parts of fuel of the condensation product described in Example 11.

EXAMPLE C

A solvent-refined, neutral SAE 10 mineral oil containing 5% of the condensation product described in Example 17.

EXAMPLE D

A synthetic lubricant comprised predominantly of $C_5$–$C_9$ normal alcohol esters of a 50/50 molar mixture of adipic and glutaric acids containing 0.5% of the condensation product described in Example 3.

EXAMPLE E

A concentrate comprising 50% of the mineral oil of Example 8 and 50% of the product described in Example 13.

The lubricant and liquid fuel compositions of this invention and the condensation products of this invention and the processes for preparing these products have been specifically exemplified above to aid those skilled in the art in understanding and practicing the invention. Many obvious variations and departures from the specific disclosure will be apparent to those of skill in the art based on principles and teachings herein and in the prior art. Such variations and departures are contemplated as being within the scope of the present invention unless clearly excluded by the appended claims.

What is claimed is:

1. A method for preparing nitrogen- and oxygen-containing compositions which comprises reacting, in the presence of an acidic catalyst, (A) at least one aliphatic hydroxy compound of the formula $R^1(OH)_x$ wherein $R^1$ is an aliphatic hydrocarbon-based radical and x is an integer which is at least 1, with (B) at least one (tertiary amino) alkanol; wherein the ratio of equivalents of reagents (A):(B) is in the range of about 1:100 up to about 100:1; wherein the amount of catalyst is in the range of about 0.01 up to about 20 based on the weight of the reaction mixture of (A) and (B); and wherein the reaction is conducted at a temperature from about 140° C. up to just below the decompostion temperature of any component of the reaction mixture.

2. A method according to claim 1 wherein reagent (B) has the formula

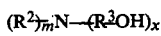

wherein
each $R^2$ is a hydrocarbon-based radical or two $R^2$ radicals taken together with the nitrogen to which each is attached to form a heterocyclic ring;
each $R^3$ is a divalent aliphatic hydrocarbon-based radical having 2–6 carbon atoms separating nitrogen from oxygen;
m is 0, 1 or 2; x is 1, 2 or 3; and m+x=3.

3. A method according to claim 1 wherein reagent (A) is at least one (tertiary amino) alkanol.

4. A method according to claim 2 wherein reagent (A), independently of reagent (B), has the formula

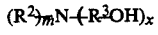

wherein
each $R^2$ is a hydrocarbon-based radical or two $R^2$ radicals taken together with the nitrogen to which each is attached to form a heterocyclic ring;
each $R^3$ is a divalent aliphatic hydrocarbon-based radical having 2–6 carbon atoms separating nitrogen from oxygen;
m is 0, 1 or 2; x is 1, 2 or 3; and m+x=3.

5. A method according to claim 2 or 4 wherein $R^3$ is an alkylene radical having from 2 up to about 25 carbon atoms and having 2 carbon atoms separating nitrogen from oxygen.

6. A method according to claim 1 or 2 wherein $R^1$ is an alkyl-based radical having from about 5 up to about 40 carbon atoms.

7. A method according to claim 6 wherein reagent (B) has the formula

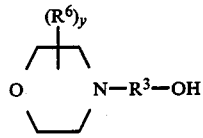

wherein $R^6$ is a lower alkyl radical of from 1 to about 4 carbon atoms and y is an integer from 0 to 4.

8. A method according to claim 5 where each $R^2$ contains from 2 up to about 40 carbon atoms.

9. A method according to claim 8 wherein each $R^2$ is alkyl, aryl, alkaryl or arylalkyl having from about 8 up to about 25 carbon atoms.

10. A method according to claim 9 wherein reagent (B) has the formula

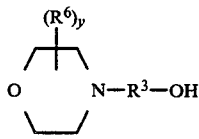

wherein $R^6$ is a lower alkyl radical of from 1 to about 4 carbon atoms and y is an integer from 0 to 4.

11. A method according to claim 5 wherein each $R^2$ is from about 40 up to about 300 carbon atoms.

12. A method according to claim 11 wherein $R^2$ contains from about 50 up to about 250 aliphatic carbon atoms.

13. A method according to claim 12 wherein reagent (B) has the formula

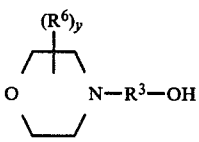

wherein $R^6$ is a lower alkyl radical of from 1 to about 4 carbon atoms and y is an integer from 0 to 4.

14. A method according to claim 12 where the reaction temperature is from about 140° C. up to just below the decomposition temperature of any component of the reaction mixture.

15. A composition prepared by the method of claim 1.
16. A composition prepared by the method of claim 2.
17. A composition prepared by the method of claim 3.
18. A composition prepared by the method of claim 4.
19. A composition prepared by the method of claim 5.
20. A composition prepared by the method of claim 6.
21. A composition prepared by the method of claim 7.
22. A composition prepared by the method of claim 8.
23. A composition prepared by the method of claim 9.
24. A composition prepared by the method of claim 10.
25. A composition prepared by the method of claim 11.
26. A composition prepared by the method of claim 12.
27. A composition prepared by the method of claim 13.
28. A composition prepared by the method of claim 14.

29. An additive concentrate comprising about 20-90% of at least one composition of claim 15 and a substantially inert, normally liquid organic diluent.
30. An additive concentrate comprising about 20-90% of at least one composition of claim 16 and a substantially inert, normally liquid organic diluent.
31. An additive concentrate comprising about 20-90% of at least one composition of claim 17 and a substantially inert, normally liquid organic diluent.
32. An additive concentrate comprising about 20-90% of at least one composition of claim 18 and a substantially inert, normally liquid organic diluent.
33. An additive concentrate comprising about 20-90% of at least one composition of claim 19 and a substantially inert, normally liquid organic diluent.
34. An additive concentrate comprising about 20-90% of at least one composition of claim 20 and a substantially inert, normally liquid organic diluent.
35. An additive concentrate comprising about 20-90% of at least one composition of claim 21 and a substantially inert, normally liquid organic diluent.
36. An additive concentrate comprising about 20-90% of at least one composition of claim 22 and a substantially inert, normally liquid organic diluent.
37. An additive concentrate comprising about 20-90% of at least one composition of claim 23 and a substantially inert, normally liquid organic diluent.
38. An additive concentrate comprising about 20-90% of at least one composition of claim 24 and a substantially inert, normally liquid organic diluent.
39. An additive concentrate comprising about 20-90% of at least one composition of claim 25 and a substantially inert, normally liquid organic diluent.
40. An additive concentrate comprising about 20-90% of at least one composition of claim 26 and a substantially inert, normally liquid organic diluent.
41. An additive concentrate comprising about 20-90% of at least one composition of claim 27 and a substantially inert, normally liquid organic diluent.
42. An additive concentrate comprising about 20-90% of at least one composition of claim 28 and a substantially inert, normally liquid organic diluent.
43. A fuel composition comprising a major amount of a normally liquid fuel and a minor amount of at least one composition of claim 15.

* * * * *